United States Patent
Bouyssou et al.

(10) Patent No.: US 7,511,067 B2
(45) Date of Patent: Mar. 31, 2009

(54) 3-HYDROXYMETHYL-4-HYDROXY-PHENYL-DERIVATIVES FOR THE TREATMENT OF RESPIRATORY DISEASES

(75) Inventors: Thierry Bouyssou, Mietingen (DE); Frank Buettner, Attenweiler (DE); Ingo Konetzki, Warthausen (DE); Sabine Pestel, Attenweiler (DE); Andreas Schnapp, Biberach (DE); Hermann Schollenberger, Ingelheim (DE); Kurt Schromm, Ingelheim (DE); Claudia Heine, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 442 days.

(21) Appl. No.: 11/028,264

(22) Filed: Jan. 3, 2005

(65) Prior Publication Data
US 2005/0234112 A1 Oct. 20, 2005

(30) Foreign Application Priority Data
Jan. 9, 2004 (DE) .................. 10 2004 001 413

(51) Int. Cl.
*A61K 31/415* (2006.01)
*C07D 233/00* (2006.01)
(52) U.S. Cl. .................. 514/385; 548/300.1
(58) Field of Classification Search .................. 514/385; 548/300.1

See application file for complete search history.

(56) References Cited

U.S. PATENT DOCUMENTS 4,378,361 A * 3/1983 Schromm et al. ........ 514/266.3
4,647,563 A * 3/1987 Schromm et al. ........ 514/230.5

OTHER PUBLICATIONS

International Search Report for PCT/EP2005/000011 mailed May 2, 2005.

* cited by examiner

*Primary Examiner*—Rei-Tsang Shiao
*Assistant Examiner*—Susannah Chung
(74) *Attorney, Agent, or Firm*—Michael P. Morris; Mary-Ellen M. Devlin; Thomas C. Blankinship

(57) ABSTRACT

The present invention relates to the use of the compounds of general formula 1

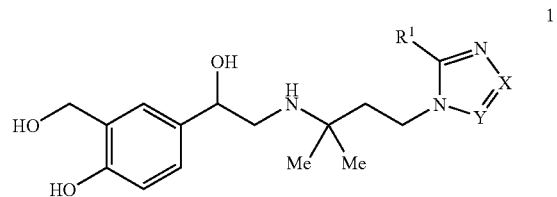

wherein the groups $R^1$, X and Y may have the meanings given in the claims and in the specification, for preparing a pharmaceutical composition for the treatment of COPD (chronic obstructive pulmonary disease), as well as new compounds of general formula 1 and processes for preparing them.

6 Claims, No Drawings

3-HYDROXYMETHYL-4-HYDROXY-PHENYL-DERIVATIVES FOR THE TREATMENT OF RESPIRATORY DISEASES

The present invention relates to compounds of general formula 1

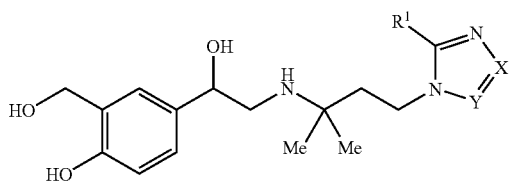

wherein the groups $R^1$, X and Y may have the meanings given in the claims and in the specification, processes for preparing them and their use as pharmaceutical compositions, particularly for the treatment of inflammatory and obstructive respiratory complaints.

BACKGROUND TO THE INVENTION

Betamimetics (β-adrenergic substances) are known from the prior art. In this respect reference is made for example to the disclosure of U.S. Pat. No. 4,647,563, which proposes betamimetics for the treatment of a wide range of diseases.

For the drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the wellbeing of the patient to a high degree. It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which are characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. A further objective of the invention is to prepare new betamimetics which, by virtue of their long-lasting effect, can be used to prepare a drug for administration once a day for the treatment of inflammatory or obstructive respiratory complaints.

In addition to the above objectives, the present invention also sets out to provide betamimetics which are not only exceptionally potent but are also characterised by a high degree of selectivity with respect to the $β_2$-adreno-receptor.

DETAILED DESCRIPTION OF THE INVENTION

Surprisingly it has been found that the above-mentioned objectives are achieved by compounds of general formula 1.

Accordingly, the present invention relates to compounds of general formula 1

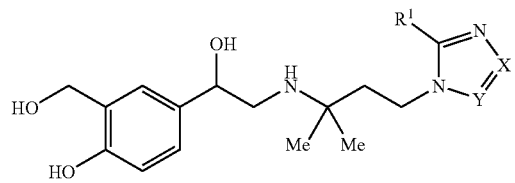

wherein
X denotes nitrogen, oxygen or $CR^2$;
Y denotes nitrogen, oxygen or $CR^3$;
$R^1$ denotes hydrogen, $C_1$-$C_4$-alkyl, halogen, OH or —O—$C_1$-$C_4$-alkyl;
$R^2$ denotes hydrogen, $C_1$-$C_4$-alkyl, halogen, OH or —O—$C_1$-$C_4$-alkyl,
or
phenyl, which may optionally be mono-, di- or trisubstituted by one or more groups selected from among $C_1$-$C_4$-alkyl, halogen, OH or —O—$C_1$-$C_4$-alkyl;
$R^3$ denotes hydrogen, $C_1$-$C_4$-alkyl, halogen, OH or —O—$C_1$-$C_4$-alkyl;
or
$R^2$ and $R^3$ together denote a bridging group —CH=CH—CH=CH, wherein one, two or three hydrogen atoms are substituted by a group selected from among $C_1$-$C_4$-alkyl, OH, halogen and —O—$C_1$-$C_4$-alkyl, with the proviso that $R^1$ cannot be hydrogen if the groups R2 and $R^3$ denote hydrogen, optionally in the form of the individual optical isomers, mixtures of the individual enantiomers or racemates, in the form of the free bases or of the corresponding acid addition salts with pharmacologically harmless acids.

Preferred compounds of general formula 1 are those wherein
X denotes nitrogen or $CR^2$;
Y denotes nitrogen or $CR^3$;
$R^1$ denotes hydrogen, methyl, ethyl, fluorine, chlorine, bromine, OH or methoxy, preferably hydrogen or methyl;
$R^2$ denotes methyl, fluorine, chlorine, bromine, OH or methoxy
or
phenyl, which may optionally be mono- or disubstituted by one or more groups selected from among methyl, fluorine, chlorine, bromine, OH or methoxy;
$R^3$ denotes hydrogen, methyl, fluorine, chlorine, bromine, OH or methoxy, optionally in the form of the individual optical isomers, mixtures of the individual enantiomers or racemates, in the form of the free bases or of the corresponding acid addition salts with pharmacologically harmless acids.

Also preferred are the above compounds of general formula 1, wherein
X denotes $CR^2$;
Y denotes nitrogen;
$R^1$ denotes hydrogen, methyl or ethyl;
$R^2$ denotes phenyl, which may optionally be mono- or disubstituted by one or more groups selected from among methyl, fluorine, chlorine, bromine, OH or methoxy;

optionally in the form of the individual optical isomers, mixtures of the individual enantiomers or racemates, in the form of the free bases or of the corresponding acid addition salts with pharmacologically harmless acids.

Also preferred are compounds of general formula 1, wherein
X denotes $CR^2$;
Y denotes nitrogen;
$R^1$ denotes hydrogen, methyl or ethyl;
$R^2$ denotes phenyl, which may be mono- or disubstituted by methyl, fluorine or methoxy;

optionally in the form of the individual optical isomers, mixtures of the individual enantiomers or racemates, in the form of the free bases or of the corresponding acid addition salts with pharmacologically harmless acids.

Particularly preferred are compounds of general formula 1, wherein
X denotes nitrogen or $CR^2$;
Y denotes nitrogen or $CR^3$;
$R^1$ denotes hydrogen or methyl, preferably hydrogen;
$R^2$ denotes methyl, OH or methoxy,
or
  phenyl, which may optionally be monosubstituted by a group selected from among methyl, OH or methoxy, preferably methoxy;
$R^3$ denotes hydrogen, methyl, OH or methoxy, optionally in the form of the individual optical isomers, mixtures of the individual enantiomers or racemates, in the form of the free bases or of the corresponding acid addition salts with pharmacologically harmless acids.

Also particularly preferred are compounds of general formula 1, wherein
X denotes nitrogen or $CR^2$;
Y denotes nitrogen or $CR^3$, preferably $CR^3$;
$R^1$ denotes hydrogen;
$R^2$ denotes phenyl, which may optionally be substituted by OH or methoxy, preferably methoxy;
$R^3$ denotes hydrogen;

optionally in the form of the individual optical isomers, mixtures of the individual enantiomers or racemates, in the form of the free bases or of the corresponding acid addition salts with pharmacologically harmless acids.

By acid addition salts with pharmacologically acceptable acids are meant, for example, the salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

The compounds of general formula 1 may optionally be used in the form of the individual optical isomers, mixtures of the individual enantiomers or racemates. If the compounds are used in enantiomerically pure form, the R-enantiomers are preferably used.

Unless otherwise stated, the alkyl groups are straight-chained or branched alkyl groups having 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated, the term alkyloxy groups (or —O-alkyl groups) denotes branched and unbranched alkyl groups having 1 to 4 carbon atoms which are linked via an oxygen atom. Examples of these include: methyloxy, ethyloxy, propyloxy or butyloxy. The abbreviations MeO—, EtO—, PropO— or BuO— are used in some cases to denote the groups methyloxy, ethyloxy, propyloxy or butyloxy. Unless otherwise stated, the definitions propyloxy and butyloxy include all possible isomeric forms of the groups in question. Thus, for example, propyloxy includes n-propyloxy and iso-propyloxy, butyloxy includes iso-butyloxy, sec.butyloxy and tert.-butyloxy, etc. In some cases, within the scope of the present invention, the term alkoxy is used instead of the term alkyloxy. Accordingly, the terms methoxy, ethoxy, propoxy or butoxy may also be used to denote the groups methyloxy, ethyloxy, propyloxy or butyloxy.

Halogen within the scope of the present invention denotes fluorine, chlorine, bromine or iodine. Unless stated otherwise, fluorine, chlorine and bromine are the preferred halogens.

The compounds according to the invention may be prepared analogously to methods already known from the prior art. Suitable methods of preparation are known for example from U.S. Pat. No. 4,647,563, to the entire contents of which reference is made at this point.

The examples of synthesis described below serve to illustrate new compounds according to the invention in more detail. However, they are intended only as examples of procedures to illustrate the invention without restricting it to the subject matter described in an exemplifying capacity hereinafter.

EXAMPLE 1

4-[2-(1,1-dimethyl-3-[1,2,4]triazol-4-yl-propylamino)-1-hydroxy-ethyl]-2-hydroxymethyl-phenol

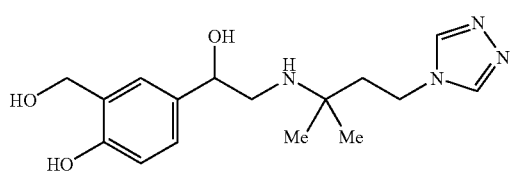

a) methyl 2-benzyloxy-5-[2-(1,1-dimethyl-3-[1,2,4]triazol-4-yl-propylimino)-acetyl]-benzoate 16 g of methyl 2-benzyloxy-5-(2-ethoxy-2-hydroxyacetyl)-benzoate and 6 g of 1,1-dimethyl-3-[1,2,4]triazol-4-yl-propylamine are heated to 70° C. for one hour in 100 mL ethanol. Then half the solvent is distilled off and the mixture remaining is cooled. The product that crystallises out is suction filtered and washed with ethanol and diethyl ether.

Yield: 15.3 g (91%); m.p.=170-172° C.

b) methyl 2-benzyloxy-5-[2-(1,1-dimethyl-3-[1,2,4]triazol-4-yl-propylamino)-acetyl]-benzoate 15.3 g of the Schiff's base are placed in 150 mL ethanol, cooled to 10° C. and combined batchwise with 1.1 g of sodium borohydride. The mixture is stirred for 2 hours at ambient temperature and then combined with 10 mL acetone. After another 30 minutes stirring a further 50 mL water are added, the mixture is acidified with glacial acetic acid and the ethanol is distilled off. The residue is combined with 100 mL water, washed twice with ethyl acetate, made alkaline with ammonia and extracted once with 150 mL ethyl acetate. The organic phase is dried with sodium sulphate and evaporated down. Yield: 14 g of yellow oil (91%).

c) 1-(4-benzyloxy-3-hydroxymethyl-phenyl)-2-(1,1-dimethyl-3-[1,2,4]triazol-4-yl-propylamino)-ethanol 5 g of calcium chloride are dissolved in 50 mL ethanol. Then 10 g of methyl 2-benzyloxy-5-[2-(1,1-dimethyl-3-[1,2,4]triazol-4-yl-propylamino)-acetyl]-benzoate in 100 mL tetrahydrofuran are added and the mixture is cooled to 5° C. It is combined batchwise with 3.5 g of sodium borohydride and stirred overnight while heating to ambient temperature. 15 mL acetone are added to the reaction mixture and it is stirred for 30 minutes. Glacial acetic acid is added, the solvents are distilled off, 100 mL water are added to the residue and it is adjusted to pH 2 with conc. hydrochloric acid. It is washed once with ethyl acetate, then made basic with ammonia, diluted with 100 mL water and extracted twice with in each case 200 mL ethyl acetate. After the organic phase has been dried it is evaporated down and the residue is dissolved in acetonitrile. The mixture is acidified with glacial acetic acid and seed crystals are added. The product precipitated is suction filtered and recrystallised from acetonitrile. Yield: 6.5 g (43%, acetate); m.p.=139-141° C.

d) 4-[2-(1,1-dimethyl-3-[1,2,4]triazol-4-yl-propylamino)-1-hydroxy-ethyl]-2-hydroxymethyl-phenol 5 g of 1-(4-benzyloxy-3-hydroxymethyl-phenyl)-2-(1,1-dimethyl-3-[1,2,4]triazol-4-yl-propylamino)-ethanol acetate are hydrogenated with 0.5 g of palladium on charcoal (5%) in 100 mL methanol. After the theoretically calculated amount of hydrogen has been taken up the catalyst is filtered off and the filtrate is evaporated down. The residue is dissolved in 10 mL ethanol and seeded. Then the product that crystallises out is suction filtered and washed. Yield: 3.2 g (74%, acetate); m.p.=125-127° C.

EXAMPLE 2

4-(1-hydroxy-2-{3-[3-(4-methoxy-phenyl)-5-methyl-[1,2,4]triazol-1-yl]-1,1-dimethyl-propylamino}-ethyl)-2-hydroxymethyl-phenol

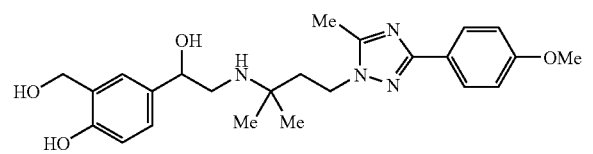

a) methyl 2-benzyloxy-5-(1-hydroxy-2-{3-[3-(4-methoxy-phenyl)-5-methyl-[1,2,4]triazol-1-yl]-1,1-dimethyl-propylamino}-ethyl)-benzoate 8.5 g of methyl 2-benzyloxy-5-(2-ethoxy-2-hydroxy-acetyl)-benzoate and 4.9 g of 3-[3-(4-methoxy-phenyl)-5-methyl-[1,2,4]triazol-1-yl]-1,1-dimethyl-propylamine in 100 mL ethanol are stirred for three hours at 60° C., cooled to 10° C., combined batchwise with 0.8 g of sodium borohydride and stirred for a further three hours at ambient temperature. Then 10 mL acetone are added and the mixture is stirred for one hour. It is then poured onto ice and acidified with glacial acetic acid. The ethanol is distilled off, the aqueous phase remaining is made alkaline with sodium hydroxide and extracted with ethyl acetate. The organic phases are dried with sodium sulphate and evaporated down. The residue is combined with 80 mL ethanol, acidified with 3.2 g of oxalic acid, dissolved in ethanol, and seeded. The product that crystallises out is suction filtered and washed. Yield: 8 g (69%, oxalate); m.p.=210-213° C.

b) 1-(4-benzyloxy-3-hydroxymethyl-phenyl)-2-{3-[3-(4-methoxy-phenyl)-5-methyl-[1,2,4]triazol-1-yl]-1,1-dimethyl-propylamino}-ethanol Analogously to the method used for Example 1c, 10 g of methyl 2-benzyloxy-5-(1-hydroxy-2-{3-[3-(4-methoxy-phenyl)-5-methyl-[1,2,4]triazol-1-yl]-1,1-dimethyl-propylamino}-ethyl)-benzoate, in 100 mL tetrahydrofuran, are reacted with a solution of 4.6 g of calcium chloride in 50 mL ethanol, as well as 3.1 g of sodium borohydride. After a reaction period of 1.5 days another 4.6 g of calcium chloride, dissolved in 50 mL ethanol, and 3.1 g of sodium borohydride are added. The reaction mixture is then worked up as described. Purification by column chromatography (CHCl$_3$/MeOH/NH$_3$=90/10/0.5) yields the product in the form of a colourless oil.

Yield: 5 g (51%); m.p. (ethyl acetate)=139-141° C.

c) 4-(1-hydroxy-2-{3-[3-(4-methoxy-phenyl)-5-methyl-[1,2,4]triazol-1-yl]-1,1-dimethyl-propylamino}-ethyl)-2-hydroxymethyl-phenol 5 g of 1-(4-benzyloxy-3-hydroxymethyl-phenyl)-2-{3-[3-(4-methoxy-phenyl)-5-methyl-[1,2,4]triazol-1-yl]-1,1-dimethyl-propylamino}-ethanol dissolved in 100 mL methanol are hydrogenated under normal pressure with 1 g of palladium on charcoal (5%) as catalyst. Then the catalyst is separated off and the filtrate is evaporated down. The residue is dissolved in 15 mL acetonitrile, acidified with 0.5 mL glacial acetic acid and seeded. The solid precipitated is filtered off and washed with acetonitrile and diethyl ether. Yield: 3.8 g (78%, acetate); m.p.=110-116° C.

EXAMPLE 3

4-(1-hydroxy-2-{3-[3-(4-methoxy-phenyl)-imidazol-1-yl-1,1-dimethyl-propylamino}-ethyl)-2-hydroxymethyl-phenol

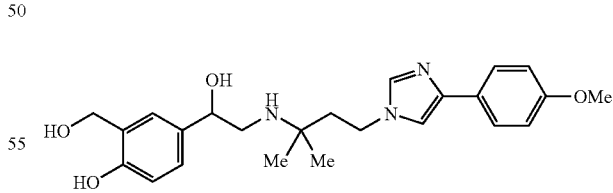

a) methyl 2-benzyloxy-5-(1-hydroxy-2-{3-[3-(4-methoxy-phenyl)-imidazol-1-yl]-1,1-dimethyl-propylamino}-ethyl)-benzoate 14 g of methyl benzyloxy-5-(2-ethoxy-2-hydroxy-acetyl)-benzoate and 7.7 g of 3-[3-(4-methoxy-phenyl)-imidazol-1-yl]-1,1-dimethyl-propylamine are reacted with 1.1 g of sodium borohydride analogously to the method used for Example 2a and worked up. After the reaction mixture has been poured onto ice and combined with glacial acetic acid, the mixture is acidified with conc. hydrochloric acid. The dihydrochloride precipitated is filtered off, washed with acetone and diethyl ether and recrystallised from 75% ethanol.

Yield: 15 g (82%, dihydrochloride); 230-232° C.

b) 1-(4-benzyloxy-3-hydroxymethyl-phenyl)-2-{3-[3-(4-methoxy-phenyl)-imidazol-1-yl]-1,1-dimethyl-propylamino}-ethanol 13 g of methyl 2-benzyloxy-5-(1-hydroxy-2-{3-[3-(4-methoxy-phenyl)-imidazol-1-yl]-1,1-dimethyl-propylamino}-ethyl)-benzoate in 100 mL tetrahydrofuran are reacted with a solution of 6.5 g of calcium chloride in 65 mL ethanol and 4.5 g of sodium borohydride analogously to the method used for Example 1c. After a reaction time of 12 hours, 3 g of calcium chloride, dissolved in 30 mL ethanol, and 2 g of sodium borohydride are added and stirring is continued for a further 12 hours. Then the mixture is worked up as described, except that extraction is carried out using chloroform rather than ethyl acetate. During the evaporation of this organic phase a solid is precipitated out. The solid is suction filtered, stirred with ethyl acetate and recrystallised from acetonitrile. Yield: 79.5 g (77%); m.p.=108-111° C.

c) 4-(1-hydroxy-2-{3-[3-(4-methoxy-phenyl)-imidazol-1-yl]-1,1-dimethyl-propylamino}-ethyl)-2-hydroxymethyl-phenol 9.4 g of 1-(4-benzyloxy-3-hydroxymethyl-phenyl)-2-{3-[3-(4-methoxy-phenyl)-imidazol-1-yl]-1,1-dimethyl-propylamino}-ethanol are dissolved in 50 mL tetrahydrofuran and 80 mL methanol and hydrogenated in the presence of 1 g of palladium on charcoal (5%). After the theoretically calculated amount of hydrogen has been taken up the catalyst is suction filtered and the filtrate is freed from solvent. The residue is dissolved in 20 mL tetrahydrofuran, acidified with 1.1 mL glacial acetic acid and combined with 1 mL water. After the addition of seed crystals the precipitated product is filtered off and washed.

Yield: 7.4 g (84%, acetate), m.p.=136-140° C.

EXAMPLE 4

4-(1-hydroxy-2-{3-[3-(4-methoxy-phenyl)-[1,2,4]triazol-1-yl]-1,1-dimethyl-propylamino}-ethyl)-2-hydroxymethyl-phenol

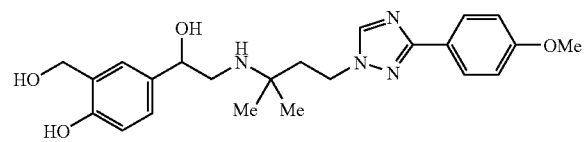

a) methyl 2-benzyloxy-5-(1-hydroxy-2-{3-[3-(4-methoxy-phenyl)-[1,2,4]triazol-1-yl]-1,1-dimethyl-propylamino}-ethyl)-benzoate The reaction and working up of 7.65 g of 2-benzyloxy-5-(2-ethoxy-2-hydroxy-acetyl)-benzoate methyl and 4.7 g of 3-[3-(4-methoxy-phenyl)-[1,2,4]triazol-1-yl]-1,1-dimethyl-propylamine are carried out analogously to the method described for Example 2a. The crude product is then converted into an oxalate in the usual way.

Yield: 8.5 g (85%, oxalate).

b) 1-(4-benzyloxy-3-hydroxymethyl-phenyl)-2-{3-[3-(4-methoxy-phenyl)-[1,2,4]triazol-1-yl]-1,1-dimethyl-propylamino}-ethanol 7.3 g of methyl 2-benzyloxy-5-(1-hydroxy-2-{3-[3-(4-methoxy-phenyl)-[1,2,4]triazol-1-yl]-1,1-dimethyl-propylamino}-ethyl)-benzoate are placed in 100 mL tetrahydrofuran and reduced with a total of 6.8 g of calcium chloride dissolved in ethanol and 4.6 g of sodium borohydride as described for Example 1c. The product is obtained after purification by column chromatography (CHCl$_3$/MeOH/NH$_3$=90/10/0.5) and subsequent recrystallisation from acetonitrile.

Yield: 4 g (58%); m.p.=120-123° C.

c) 4-(1-hydroxy-2-{3-[3-(4-methoxy-phenyl)-[1,2,4]triazol-1-yl]-1,1-dimethyl-propylamino}-ethyl)-2-hydroxymethyl-phenol 3.8 g of 1-(4-benzyloxy-3-hydroxymethyl-phenyl)-2-{3-[3-(4-methoxy-phenyl)-[1,2,4]triazol-1-yl]-1,1-dimethyl-propylamino}-ethanol are hydrogenated with 0.6 g of palladium on charcoal (5%) as catalyst in 75 mL methanol and 75 mL tetrahydrofuran. Then the catalyst is suction filtered and the filtrate is evaporated down. The residue is dissolved in 15 mL 15% m acetonitrile, acidified with formic acid and combined with a crystallisation aid. The precipitated product is separated off and washed. Yield: 2.8 g (81%, formate); m.p.=142-145° C.

EXAMPLE 5

4-[2-(1,1-dimethyl-3-[1,2,4]triazol-1-yl-propylamino)-1-hydroxy-ethyl]-2-hydroxymethyl-phenol

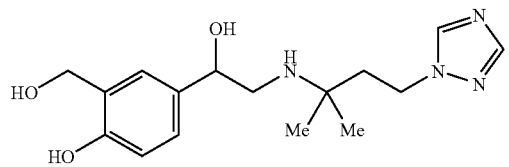

a) methyl 2-benzyloxy-5-[2-[1,1-dimethyl-3-[1,2,4]triazol-1-yl-propylamino]-1-hydroxy-ethyl]-benzoate 9.5 g of methyl 2-benzyloxy-5-(2-ethoxy-2-hydroxy-acetyl)-benzoate and 3.1 g of 1,1-dimethyl-3-[1,2,4]triazol-1-yl-propylamine are reacted and worked up analogously to the method described for Example 2a. The crude product is dissolved in 100 mL 95% ethanol and combined with an ethanolic solution of 1.8 g of oxalic acid. After the addition of a crystallisation aid the precipitated product is separated off and washed. Yield: 8 g (64%, bisoxalate), m.p.=220-222° C.

b) 1-(4-benzyloxy-3-hydroxymethyl-phenyl)-2-(1,1-dimethyl-3-[1,2,4]triazol-1-yl-propylamino)-ethanol 7.6 g of methyl 2-benzyloxy-5-[2-[1,1-dimethyl-3-[1,2,4]triazol-1-yl-propylamino]-1-hydroxy-ethyl]-benzoate are reduced in an ethanolic calcium chloride solution with sodium borohydride as described for Example 1c. The product is obtained as a colourless oil after purification by column chromatography (CHCl$_3$/MeOH/NH$_3$=90/10/0.5). Yield: 6 g (84%).

c) 4-[2-(1,1-dimethyl-3-[1,2,4]triazol-1-yl-propylamino)-1-hydroxy-ethyl]-2-hydroxymethyl-phenol The debenzylation of 6 g of 1-(4-benzyloxy-3-hydroxymethyl-phenyl)-2-(1,1-dimethyl-3-[1,2,4]triazol-1-yl-propylamino)-ethanol is carried out hydrogenolytically with 1 g of palladium on charcoal (5%) in 100 mL methanol. After the catalyst has been removed by suction filtering and the filtrate has been evaporated down the residue is dissolved in 20 mL 90% ethanol, combined with sulphuric acid and seeded. The precipitated product is filtered off and washed. Yield: 3 g (55%, hemisulphate); m.p.=177-180° C.

The compounds according to the invention of Examples 6-9 were also obtained using the methods of synthesis described below.

Synthesis of the Precursors for Examples 6-9:

Precursor 1) 1,1-dimethyl-3-(5-methyl-3-yl-tolyl-[1,2,4]triazol-1-yl]-propylamine

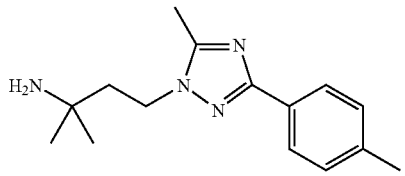

P-1-a) 4-methyl-benzoic acid-(1-imino-ethyl)-hydrazide 1.65 g (72 mmol) of sodium are dissolved in 80 mL ethanol. 8.89 g (72 mmol) of ethylacetimidate hydrochloride in 160 mL ethanol are added at ambient temperature and the precipitated sodium chloride is filtered off. The filtrate is combined with 6.00 g (40 mmol) 4-methyl-benzoic acid hydrazide and stirred overnight. The reaction mixture is evaporated down and cooled. The precipitated solid is filtered off and washed with cold ethanol and diethyl ether (5.7 g of white solid). A further 1.2 g of solid are obtained from the filtrate after the removal of the solvent by distillation and recrystallisation from ethanol. Yield: 6.93 g (91%); mass spectroscopy [M+H]$^+$=192.

P-1-b) 5-methyl-3-p-tolyl-[1,2,4]triazole 7.58 g (40 mmol) 4-methyl-benzoic acid-(1-imino-ethyl)-hydrazide are heated to 180° C. for 30 minutes with stirring. After cooling the solid is dissolved in chloroform. The precipitate formed on cooling is suction filtered and recrystallised from chloroform.
Yield: 4.82 g (70%); mass spectroscopy [M+H]$^+$=174.

P-1-c) tert.butyl [1,1-dimethyl-3-(5-methyl-3-p-tolyl-[1,2,4]triazol-1-yl)-propyl]-carbamate 1.35 g (34 mmol, 60%) sodium hydride are added to a solution of 4.87 g (28 mmol) of 5-methyl-3-p-tolyl-[1,2,4]triazole in 40 mL DMPU at 0° C. The reaction mixture is heated to ambient temperature and then stirred for one hour. 9.35 g (42 mmol) of tert.butyl (3-chloro-1,1-dimethyl-propyl)-carbamate and 1.87 g (5 mmol) of tetrabutylammonium iodide are added and the mixture is stirred overnight at ambient temperature and then for 2 hours at 80° C. It is combined with water and ethyl acetate, the aqueous phase is separated off and extracted with ethyl acetate. The combined organic phases are washed with water and sodium chloride solution, dried with sodium sulphate and evaporated down. The residue is purified by column chromatography (silica gel; petroleum ether/ethyl acetate=1.1). Oil.
Yield: 2.97 g (30%); mass spectroscopy [M+H]$^+$=359.

P-1-d) 1,1-dimethyl-3-(5-methyl-3-p-tolyl-[1,2,4]triazol-1-yl]-propylamine

A total of 11 mL trifluoroacetic acid are added dropwise to a solution of 2.97 g (8.3 mmol) of tert.butyl [1,1-dimethyl-3-(5-methyl-3-p-tolyl-[1,2,4]triazol-1-yl)-propyl]-carbamate in 80 mL dichloromethane and the mixture is stirred overnight at ambient temperature. The solvent is distilled off and the residue is combined with diethyl ether and stirred. The precipitated solid is filtered off and washed. Yield: 2.11 g (68%, trifluoroacetate); mass spectroscopy [M+H]$^+$=259.

Precursor 2) 3-[3-(4-fluoro-phenyl)-5-methyl-[1,2,4]triazol-1-yl]-1,1-dimethyl-propylamine

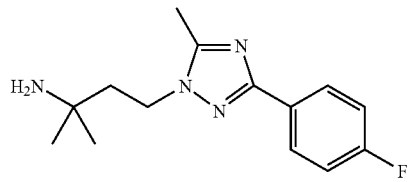

P-2-a) 4-fluoro-benzoic acid-(1-imino-ethyl)-hydrazide

Prepared from 7.2 g (58 mmol) of ethylacetimidate hydrochloride and 5.00 g (32 mmol) of 4-fluoro-benzoic acid hydrazide analogously to the method described under P-1-a).
Yield: 5.78 g (91%); mass spectroscopy [M+H]$^+$=196.

P-2-b) 3-(4-fluoro-phenyl)-5-methyl-[1,2,4]-triazole

The compound is prepared analogously to the method described in P-1-b) from 5.77 g (30 mmol) of 4-fluoro-benzoic acid-(1-imino-ethyl)-hydrazide.
Yield: 4.11 g (78%); mass spectroscopy [M+H]$^+$=178.

P-2-c) tert.butyl {3-[3-(4-fluoro-phenyl)-5-methyl-[1,2,4]triazol-1-yl]-1,1-dimethyl-propyl}-carbamate 5.88 g (33 mmol) of 3-(4-fluoro-phenyl)-5-methyl-[1,2,4]triazole are dissolved in 40 mL DMPU and reacted with 11.04 g (50 mmol) of tert.butyl (3-chloro-1,1-dimethyl-propyl)-carbamate, 1.59 g (40 mmol, 60%) of sodium hydride and 2.21 g (6 mmol) of tetrabutylammonium iodide in the manner described in P-1-c).
Yield: 4.22 g (35%); mass spectroscopy [M+H]$^+$=363.

P-2-d) 3-[3-(4-fluoro-phenyl)-5-methyl-[1,2,4]triazol-1-yl]-1,1-dimethyl-propylamine Obtained by reacting 4.22 g (11.6 mmol) of tert.butyl {3-[3-(4-fluoro-phenyl)-5-methyl-[1,2,4]triazol-1-yl]-1,1-dimethyl-propyl}-carbamate in 100 mL dichloromethane and 15 mL trifluoroacetic acid. White solid.
Yield: 4.43 g (trifluoroacetate); mass spectroscopy [M+H]$^+$=263.

Precursor 3) 3-[3-(3,5-difluoro-phenyl)-5-methyl-[1,2,4]triazol-1-yl]-1,1-dimethyl-propylamine

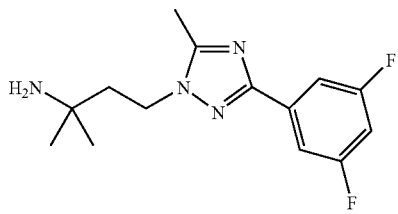

P-3-a) 3,5-difluoro-benzoic acid-(1-imino-ethyl)-hydrazide

Obtained from 4.91 g (40 mmol) of ethylacetimidate hydrochloride and 3.80 g (22 mmol) of 3,5 difluoro-benzoic acid hydrazide analogously to the method described in P-1-a). Yield: 4.49 g (95%); mass spectroscopy $[M+H]^+=214$.

P-3-b) 3-(3,5-difluoro-phenyl)-5-methyl-[1,2,4]triazole

Prepared from 4.61 g (22 mmol) of 3,5-difluoro-benzoic acid-(1-imino-ethyl)-hydrazide.
Yield: 3.81 g (91%); mass spectroscopy $[M+H]^+=196$.

P-3-c) tert.butyl {3-[3-(3,5-difluoro-phenyl)-5-methyl-[1,2,4]triazol-1-yl]-1,1-dimethyl-propyl}-carbamate 3.74 g (19 mmol) of 3-(3,5-difluoro-phenyl)-5-methyl-[1,2,4]triazole in 25 mL DMPU are reacted with 0.92 g (23 mmol, 60%) of sodium hydride, 6.37 g (29 mmol) of tert.butyl (3-chloro-1,1-dimethyl-propyl)-carbamate and 1.27 g (3.5 mmol) of tetrabutylammonium iodide analogously to P-1-c). Oil.
Yield: 2.62 g (36%); mass spectroscopy $[M+H]^+=381$.

P-3-d) 3-[3-(3,5-difluoro-phenyl)-5-methyl-[1,2,4]triazol-1-yl]-1,1-dimethyl-propylamine 2.62 g (6.9 mmol) of tert.butyl {3-[3-(3,5-difluoro-phenyl)-5-methyl-[1,2,4]triazol-1-yl]-1,1-dimethyl-propyl}-carbamate in 65 mL dichloromethane are reacted with 9 mL trifluoroacetic acid in the manner described in P-1-d). White solid.
Yield: 2.11 g (trifluoroacetate); mass spectroscopy $[M+H]^+=281$.

Precursor 4) 3-[5-ethyl-3-(4-methoxy-phenyl)-[1,2,4]triazol-1-yl]-1,1-dimethyl-propylamine

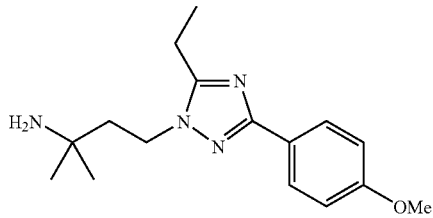

P-4-a) 4-methoxy-benzoic acid-(1-imino-propyl)-hydrazide

Prepared from 4.90 g (45 mmol) of propioamidine hydrochloride and 5.00 g (30 mmol) of 4-methoxy-benzoic acid hydrazide analogously to the method described in P-1-a).

After the ethanol has been distilled off 10.0 g of crude product are obtained which are reacted without any further purification.

P-4-b) 5-ethyl-3-(4-methoxy-phenyl)-[1,2,4]triazole 9.99 g (60%, approx. 28 mmol) of 4-methoxy-benzoic acid-(1-imino-propyl)-hydrazide are heated to 150° C. for two hours. After cooling the melt is purified by chromatography on a silica gel column (petroleum ether/ethyl acetate=3/7). Light yellow solid. Yield: 4.56 g (75% over two steps); mass spectroscopy $[M+H]^+=204$.

P-4-c) tert.butyl {3-[5-ethyl-3-(4-methoxy-phenyl)-[1,2,4]triazol-1-yl]-1,1-dimethyl-propyl-carbamate 4.30 g (21.2 mmol) of 5-ethyl-3-(4-methoxy-phenyl)-[1,2,4]triazole are dissolved in 30 mL DMPU and cooled to 0° C. Then 1.02 g (24 mmol, 60%) of sodium hydride are added batchwise under a protective gas atmosphere and the reaction mixture is slowly heated to ambient temperature and then stirred one hour. 6.10 g (27.5 mmol) of tert.butyl (3-chloro-1,1-dimethyl-propyl)-carbamate and 1.41 g (3.8 mmol) of tetrabutylammonium iodide are added. The mixture is stirred overnight and then the reaction is ended by the addition of water and ethyl acetate. The aqueous phase is separated off and extracted with ethyl acetate. The combined organic phases are washed with sodium chloride solution, dried with sodium sulphate and evaporated down. The oil remaining is purified by chromatography on a silica gel column (petroleum ether/ethyl acetate=3:7).
Yield: 6.82 g (83%); mass spectroscopy $[M+H]^+=389$.

P-4-d) 3-[5-ethyl-3-(4-methoxy-phenyl)-[1,2,4]triazol-1-yl]-1,1-dimethyl-propylamine A total of 20 mL trifluoroacetic acid are added dropwise to a solution of 6.81 g (17.5 mmol) of tert.butyl {3-[5-ethyl-3-(4-methoxy-phenyl)-[1,2,4]triazol-1-yl]-1,1-dimethyl-propyl-carbamate in 150 mL dichloromethane. After three hours stirring at ambient temperature the solution is evaporated down and the oil remaining is combined with diethyl ether. The white solid precipitated is filtered off, washed with diethyl ether and dried.
Yield: 7.86 g (trifluoroacetate); mass spectroscopy $[M+H]^+=289$.

General Working Method A for Synthesising Examples 6 to 9:

1 mmol of glyoxal aldehyde or acetal and 1 mmol of amine are stirred for 15 minutes in 5 mL tetrahydrofuran at 60° C. The mixture is cooled to 0° C. and under an argon atmosphere 2 mL of a 2 molar solution of lithium borohydride in tetrahydrofuran are added dropwise thereto. The mixture is stirred for 15 min at 0° C., then heated to ambient temperature and a further 2 mL of the lithium borohydride solution are added. After 5 hours at 50° C. 10 mL dichloromethane and 3 mL water are added, the mixture is stirred for 30 minutes at ambient temperature and then filtered through diatomite, eluting with dichloromethane and methanol. The eluate is freed from solvent and if necessary the residue is purified by chromatography. The benzylether thus obtained is dissolved in methanol and hydrogenated with palladium on charcoal (10%) as catalyst at normal pressure and ambient temperature. Then the catalyst is separated off and the crude product is purified by chromatography (reverse phase, acetonitrile/water gradient) or recrystallised from acetonitrile.

EXAMPLE 6

4-{2-[1,1-dimethyl-3-(5-methyl-3-p-tolyl-[1,2,4]triazol-1-yl)-propylamino]-1-hydroxy-ethyl}-2-hydroxymethyl-phenol

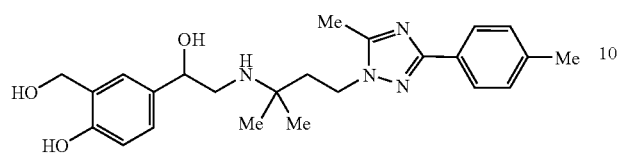

The compound is prepared analogously to the general working method A from 241 mg (0.7 mmol) of methyl 2-benzyloxy-5-(2-ethoxy-2-hydroxy-acetyl)-benzoate and 181 mg (0.7 mmol) of 1,1-dimethyl-3-(5-methyl-3-p-tolyl-[1,2,4]triazol-1-yl)-propylamine.

Yield: 13 mg (4%); mass spectroscopy [M+H]$^+$=425.

EXAMPLE 7

4-(2-{3-[3-(3,5-difluoro-phenyl)-5-methyl-[1,2,4]triazol-1-yl]-1,1-dimethyl-propylamino}-1-hydroxy-ethyl)-2-hydroxymethyl-phenol

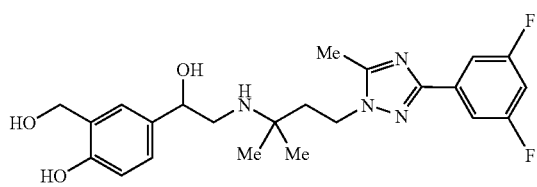

The compound is obtained according to general working method A from 121 mg (0.35 mmol) of methyl 2-benzyloxy-5-(2-ethoxy-2-hydroxy-acetyl)-benzoate and 98 mg (0.35 mmol) of 3-[3-(3,5-difluoro-phenyl)-5-methyl-[1,2,4]triazol-1-yl]-1,1-dimethyl-propylamine. Yield: 9 mg (6%); mass spectroscopy [M+H]$^+$=447.

EXAMPLE 8

4-(2-{3-[3-(4-fluoro-phenyl)-5-methyl-[1,2,4]triazol-1-yl]-1,1-dimethyl-propylamino}-1-hydroxy-ethyl)-2-hydroxymethyl-phenol

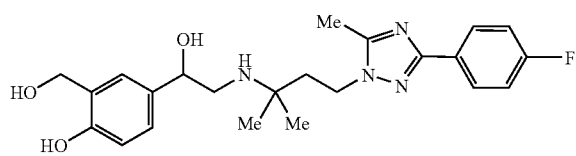

Prepared according to general working method A from 344 mg (1 mmol) of methyl 2-benzyloxy-5-(2-ethoxy-2-hydroxy-acetyl)-benzoate and 262 mg (1 mmol) of 3-[3-(4-fluoro-phenyl)-5-methyl-[1,2,4]triazol-1-yl]-1,1-dimethyl-propylamine.

Yield: 8 mg (2%); mass spectroscopy [M+H]$^+$=429.

EXAMPLE 9

4-(2-{3-[5-ethyl-3-(4-methoxy-phenyl)-[1,2,4]triazol-1-yl]-1,1-dimethyl-propylamino}-1-hydroxy-ethyl)-2-hydroxymethyl-phenol

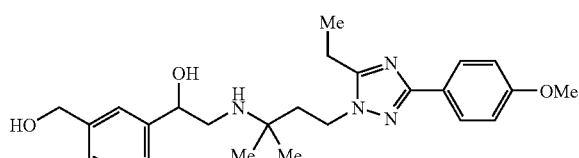

The compound is prepared analogously to the general working method A from 344 mg (1 mmol) of methyl 2-benzyloxy-5-(2-ethoxy-2-hydroxy-acetyl)-benzoate and 262 mg (1 mmol) of 3-[5-ethyl-3-(4-methoxy-phenyl)-[1,2,4]triazol-1-yl]-1,1-dimethyl-propylamine. The debenzylation is carried out with Raney nickel as catalyst at 3 bar and ambient temperature in ethanol. During the final purification by chromatography 0.1% trifluoroacetic acid is added to the eluant (acetonitrile/water gradient).

Yield: 102 mg (18%, trifluoroacetate); mass spectroscopy [M+H]$^+$=455.

As has been found, the compounds of general formula 1 are characterised by their range of uses in the therapeutic field. Particular mention should be made of those applications for which the compounds of formula 1 according to the invention may preferably be used on the basis of their pharmaceutical activity as betamimetics.

These include, for example, the treatment of inflammatory and obstructive respiratory complaints, preferably the treatment of asthma or COPD (chronic obstructive pulmonary disease), the inhibition of premature labour in midwifery (tocolysis), the restoration of the sinus rhythm in the heart in cases of atrio-ventricular block as well as the correcting of bradycardiac heart rhythm disorders (antiarrhythmic agent), the treatment of circulatory shock (vasodilatation and increasing the heart-time volume) as well as the treatment of itching and skin inflammation.

In one aspect the present invention relates to the use of the compounds of general formula 1 as pharmaceutical compositions. In another aspect the present invention relates to the use of the compounds of general formula 1 for preparing a pharmaceutical composition for the treatment of diseases, wherein therapeutically effective doses of a betamimetic can deliver a therapeutic benefit. It is particularly preferable to use compounds of general formula 1 for preparing a pharmaceutical composition for the treatment of inflammatory and obstructive respiratory complaints, particularly preferably the treatment of asthma or COPD, for inhibiting premature labour in midwifery (tocolysis), for restoring the sinus rhythm in the heart in cases of atrio-ventricular block, for correcting bradycardiac heart rhythm disorders, for treating circulatory shock (vasodilatation and increasing the heart-time volume) and for the treatment of itching and skin inflammation. It is particularly preferred according to the invention to use compounds of general formula 1 for preparing a pharmaceutical composition for the treatment of inflammatory and obstructive respiratory complaints, particularly preferably for the treatment of asthma or COPD. Also of particular importance is the use of compounds of general formula 1 as described above for preparing a pharmaceutical composition for a once-a-day treatment of inflammatory and obstructive respiratory complaints, particularly preferably for a once-a-day treatment of asthma or COPD.

The compounds of general formula 1 may be used on their own or in conjunction with other active substances of formula 1 according to the invention. The compounds of general formula 1 may optionally also be used in combination with other pharmacologically active substances. These may be, in particular, anticholinergics, possibly other betamimetics, antiallergics, PDE-IV inhibitors, PAF antagonists, leukotriene antagonists and steroids as well as combinations of active substances thereof.

Examples of anticholinergics which may be mentioned are ipratropium bromide, oxitropium bromide and particularly tiotropium bromide. Drug combinations which contain tiotropium bromide, optionally in the form of one of its solvates or hydrates, as another active substance in addition to the compounds of formula 1 according to the invention are particularly preferred according to the invention. Tiotropium bromide is particularly preferably used in the form of its monohydrate, particularly in the form of its crystalline monohydrate. This crystalline monohydrate is described in detail in WO 02/30928.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide and dexamethasone. Preferably, within the scope of the present invention, the corticosteroids are selected from among flunisolide, beclomethasone, triamcinolone, budesonide, fluticasone, mometasone, ciclesonide and dexamethasone, while in this instance budesonide, fluticasone, mometasone and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. In some cases the corticosteroids may also occur in the form of their hydrates.

Within the scope of the present invention, the term dopamine agonists, which may optionally be used in conjunction with the compounds of formula 1, denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use, as combination partners with the compound of formula 1, dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the above-mentioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of antiallergic agents which may be used according to the invention as a combination with the compound of formula 1 include epinastin, cetirizin, azelastin, fexofenadin, levocabastin, loratadine, mizolastin, ketotifen, emedastin, dimetinden, clemastine, bamipin, cexchlorpheniramine, pheniramine, doxylamine, chlorophenoxamine, dimenhydrinate, diphenhydramine, promethazine, ebastin, desloratidine and meclizine. Preferred antiallergic agents which may be used within the scope of the present invention in combination with the compounds of formula 1 according to the invention are selected from among epinastin, cetirizin, azelastin, fexofenadin, levocabastin, loratadine, ebastin, desloratidine and mizolastin, epinastin and desloratidine being particularly preferred. Any reference to the above-mentioned antiallergic agents also includes, within the scope of the present invention, a reference to any pharmacologically acceptable acid addition salts thereof which may exist.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A and AWD-12-281. Preferred PDE-IV inhibitors are selected from among enprofylline, roflumilast, ariflo and AWD-12-281, while AWD-12-281 is particularly preferred as the combination partner with the compound of formula 1 according to the invention. Any reference to the above-mentioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. According to the invention, the salts selected from among the acetate, hydrochloride, hydrobromide, sulphate, phosphate and methanesulphonate are preferred in this context.

Suitable preparations for administering the compounds of formula 1 include for example tablets, capsules, suppositories, solutions, powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

In the preferred use of the compounds of formula 1 for the treatment of asthma or COPD according to the invention it is particularly preferred to use preparations or pharmaceutical formulations which are suitable for inhalation. Inhalable preparations include inhalable powders, propellant-containing metered-dose aerosols or propellant-free inhalable solutions Within the scope of the present invention, the term propellant-free inhalable solutions also includes concentrates or sterile ready-to-use inhalable solutions. The formulations which may be used within the scope of the present invention are described in more detail in the next part of the specification The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 μm, more preferably from 1 to 5 μm, is added to the excipient mixture. Processes for producing the inhalable powders according to the invention by grinding and micronising and lastly mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example.

In another aspect the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

Examples of Pharmaceutical Formulations

| A) | Tablets | per tablet |
|---|---|---|
| | active substance 1 | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance 1 | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance 1 | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| D) | Metering aerosol | |
|---|---|---|
| | Active substance 1 | 0.005 |
| | Sorbitan trioleate | 0.1 |
| | Monofluorotrichloromethane and T134a:TG227 | ad 100 |

The suspension is transferred into a conventional aerosol container with a metering valve. Preferably, 50 µl of suspension are delivered per spray. The active substance may also be metered in higher doses if desired (e.g. 0.02% by weight).

| E) | Solutions (in mg/100 ml) | |
| --- | --- | --- |
| | Active substance 1 | 333.3 mg |
| | Tiotropium bromide | 333.3 mg |
| | Benzalkonium chloride | 10.0 mg |
| | EDTA | 50.0 mg |
| | HCl (1n) | ad pH 3.4 |

This solution may be prepared in the usual manner.

| F) | Powder for inhalation | |
| --- | --- | --- |
| | Active substance 1 | 6 μg |
| | Tiotropium bromide monohydrate | 6 μg |
| | Lactose monohydrate | ad 25 mg |

The powder for inhalation is produced in the usual way by mixing the individual ingredients together.

The invention claimed is:

1. A compound of formula 1

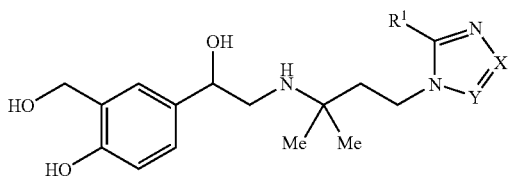

wherein
X denotes nitrogen or CR²;
Y denotes nitrogen or CR³;
R¹ denotes hydrogen;
R² denotes phenyl, which may optionally be substituted by OH or methoxy;
R³ denotes hydrogen;
an individual optical isomer, a mixture of the individual enantiomers or a racemate, in the form of the free base or of the corresponding acid addition salt with a pharmacologically acceptable acid.

2. A compound of formula 1,

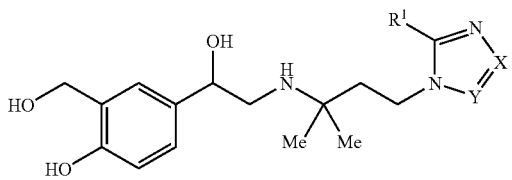

wherein
X denotes CR²;
Y denotes nitrogen;
R¹ denotes hydrogen, methyl or ethyl;
R² denotes phenyl, which may optionally be mono- or disubstituted by one or more groups selected from among methyl, fluorine, chlorine, bromine, OH or methoxy
an individual optical isomer, a mixture of the individual enantiomers or a racemate, in the form of the free base or of the corresponding acid addition salt with a pharmacologically acceptable acid.

3. A compound of formula 1,

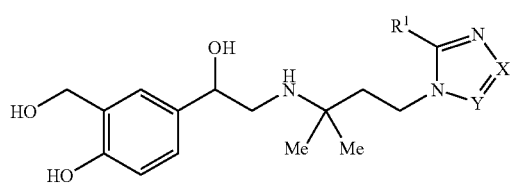

wherein
X denotes CR²;
Y denotes nitrogen;
R¹ denotes hydrogen, methyl or ethyl;
R² denotes phenyl, which may be mono- or disubstituted by methyl, fluorine, or methoxy;
an individual optical isomer, a mixture of the individual enantiomers or a racemate, in the form of the free base or of the corresponding acid addition salt with a pharmacologically acceptable acid.

4. A pharmaceutical composition comprising a compound according to claim 1 and a pharmaceutically acceptable carrier or excipient.

5. A pharmaceutical composition comprising a compound according to claim 2 and a pharmaceutically acceptable corner or excipient.

6. A pharmaceutical composition comprising a compound according to claim 3 and a pharmaceutically acceptable corner or excipient.

* * * * *